United States Patent
Suurmond et al.

(10) Patent No.: US 7,020,510 B2
(45) Date of Patent: Mar. 28, 2006

(54) OPTIMAL VIEW MAP V.0.01

(75) Inventors: Rudolf Theodoor Suurmond, Eindhoven (NL); Onno Wink, Denver, CO (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 403 days.

(21) Appl. No.: 10/205,559

(22) Filed: Jul. 25, 2002

(65) Prior Publication Data

US 2004/0019264 A1  Jan. 29, 2004

(51) Int. Cl.
*A61B 5/05* (2006.01)

(52) U.S. Cl. .................................................. 600/425

(58) Field of Classification Search ................ 600/425, 600/413, 419; 711/100; 712/220; 434/262
See application file for complete search history.

(56) References Cited

U.S. PATENT DOCUMENTS

| | | | | |
|---|---|---|---|---|
| 4,977,505 A | * | 12/1990 | Pelizzari et al. | 600/425 |
| 5,431,161 A | * | 7/1995 | Ryals et al. | 600/425 |
| 5,531,227 A | * | 7/1996 | Schneider | 600/425 |
| 5,951,475 A | * | 9/1999 | Gueziec et al. | 600/425 |
| 6,240,308 B1 | * | 5/2001 | Hardy et al. | 600/407 |
| 6,466,813 B1 | * | 10/2002 | Shukla et al. | 600/411 |

OTHER PUBLICATIONS

S. Chen et al., "3-D Reconstruction off Coronary Arterial Tree to Optimize Angiographic Visualization", IEEE Transactions on Medical Imaging, vol. 19, No. 4, Apr. 2000.
S. Chen et al., "Computer Assisted Coronary Intervention by Use of On-Line 3-D Reconstruction and Optimal View Strategy", MICCAI 1998: 377-385.

(Continued)

*Primary Examiner*—Daniel Robinson (57) ABSTRACT

A method is disclosed which allows for optimally viewing a portion of a patient vascular system to facilitate at least one of diagnosis and treatment the vascular system. The method includes acquiring a model of said vascular system based on image data generated by an imaging device, identifying a portion of interest of the vascular system including determining a central vessel axis for a vessel of interest, generating a foreshortening map of the portion of interest based on viewing angle of the imaging device position, with respect to the patient, generating an overlap map to determine an amount of overlap present for particular viewing angles based on imaging device position, and generating a feasibility map to model dimensions of the patient based on patient characteristics, imaging device configuration, foreshortening and overlap.

7 Claims, 13 Drawing Sheets

OTHER PUBLICATIONS

J. Bruijns, "Semi-Automatic Shape Extraction from Tube-like Geometry", Article, Conference: Vision, Modeling and Visualization, Germany 2000.

J. Bruijns, "Fully-Automatic Branch Labeling of Voxel Vessel Structures", Conference Article.

"Minimum Cost Path Determination Using a Simple Heuristic Function", by Onno Wink et al, Image Sciences Institute (ISI) University Medical Center Utrecht, The Netherlands.

"A Viewpoint Determination System for Stenosis Diagnosis and Quantification in Coronary Angiographic Image Acquisition", by Y. Sato et al. IEEE Trans. on Medical Imaging, vol. 17, No. 1, pp. 53-54 (1995).

"Optimizing Coronary Angiographic Views", Int. Journal Cardiac Imaging, vol. 1, pp. 53-54 (1995).

3-D Coronary Angiography: Improving Visualization Strategy for Coronary Interventions, What's New in Cardiovascular Imaging, Kluwer Academic Publishers, pp. 61-67, (1998).

* cited by examiner

Fig. 1(A)

PRIOR ART

Fig. 1(B)

PRIOR ART

Fig. 2(a)

PRIOR ART

Fig 2(b)

PRIOR ART

Fig 2(c)

PRIOR ART

Fig 3(a)

PRIOR ART

Fig. 3(b)

PRIOR ART

Fig. 3(c)

PRIOR ART

OPTIMAL VIEW MAP V.0.01

BACKGROUND OF THE INVENTION

The invention is directed to optimal view strategies for cardiac interventional treatment planning, and, more particularly relates to the generation and use of a feasibility map for modeling vascular characteristics of a patient in view of physical constraints, such as a 3D coronary artery tree, prior to and/or concurrently with intervention.

Quantitative description of the coronary arterial tree including geometry is required for diagnosis and prognosis of coronary disease, as well as for performance of catheter-based coronary interventions. Many computer-assisted techniques for estimation of the three-dimensional (3-D) coronary arteries from biplane projection are known in the art. However, due to the problem of vessel overlap and foreshortening, multiple projections are necessary to adequately evaluate the coronary arterial tree with arteriography. The elimination or at least minimization of foreshortening and overlap is a prerequisite for an accurate quantitative coronary analysis (QCA), such as determination of intercoronary lengths in a 2-D display.

Optimal view maps (OVMS) are known in the art. OVMs aid a user in obtaining a gantry position of the imaging device which results in an optimal view; OVMs were devised in an effort to remove the subjective nature of minimizing foreshortening and overlap. For example, G. Finet and J. Lienard, OPTIMIZING CORONARY ANGIOGRAPHIC VIEWS, Int. Journal Cardiac Imaging, Supplement 1, vol. 1, pp. 53–54, 1995, focused only on minimization of vessel foreshortening relative to a single arterial segment.

Y. Sato, et al., A VIEWPOINT DETERMINATION SYSTEM FOR STENOSIS DIAGNOSIS AND QUANTIFICATION IN CORONARY ANGIOGRAPHIC ACQUISITION, IEE Tran. On Medical Imaging, vol. 17, no. 1, pp. 53–54, 1995, and S. J. Chen and J. D. Caroll, 3-D CORONARY ANGIOGRAPHY: IMPROVING VISUALIZATION STRATEGY FOR CORONARY INTERVENTIONS, Whats New In Cardiovascular Imaging, Kluwer Academic Publishers, pp. 61–67, 1998 (Chen and Carroll I), discuss derivation of an optimal view strategy on the basis of minimization of both vessel overlap and foreshortening. However, the technique devised by Sato requires a well-calibrated imaging system and manually specified correspondence in the 3-D reconstruction process. Additionally, the overlap measurement is limiting because it is performed based on the single stenotic segment with only immediate adjacent vessels. Sub-optimal solutions in determining optimal view are ineffective when the segment was more complex and more distal vessels were overlapped, both conditions of which are common in clinical conditions.

Broadly, conventional OVMs are utilized for on-line reconstruction of a 3D arterial tree based on a pair of routine angiograms acquired from any two arbitrary viewing angles using single- of bi-plane imaging systems. A conventional process for deriving an OVM requires 1) acquisition of two standard angiogram sequences by use of a single-plane imaging system; 2) identification of 2D arterial tress and feature extractions, including bifurcation points, vessel diameters, vessel directional vertices, vessel centerlines, and construction of vessel hierarchies in the two images; 3) determination of a transformation defining the spatial relationship of the acquired two views in terms of a rotation matrix and translation vector; and 4) calculation of the 3D arterial (e.g., coronary) trees arterial structures based thereon. S. J. Chen and J. D. Caroll, 3-D RECONSTRUCTION OF CORONARY ARTERIAL TREE TO OPTIMIZE ANGIOGRAPHIC VISUALIZATION, IEEE Transactions on Medical Imaging, vol. 19, no. 4, April, 2000 (hereafter "Chen and Carroll II"), incorporated herein by reference.

Figure 1A:
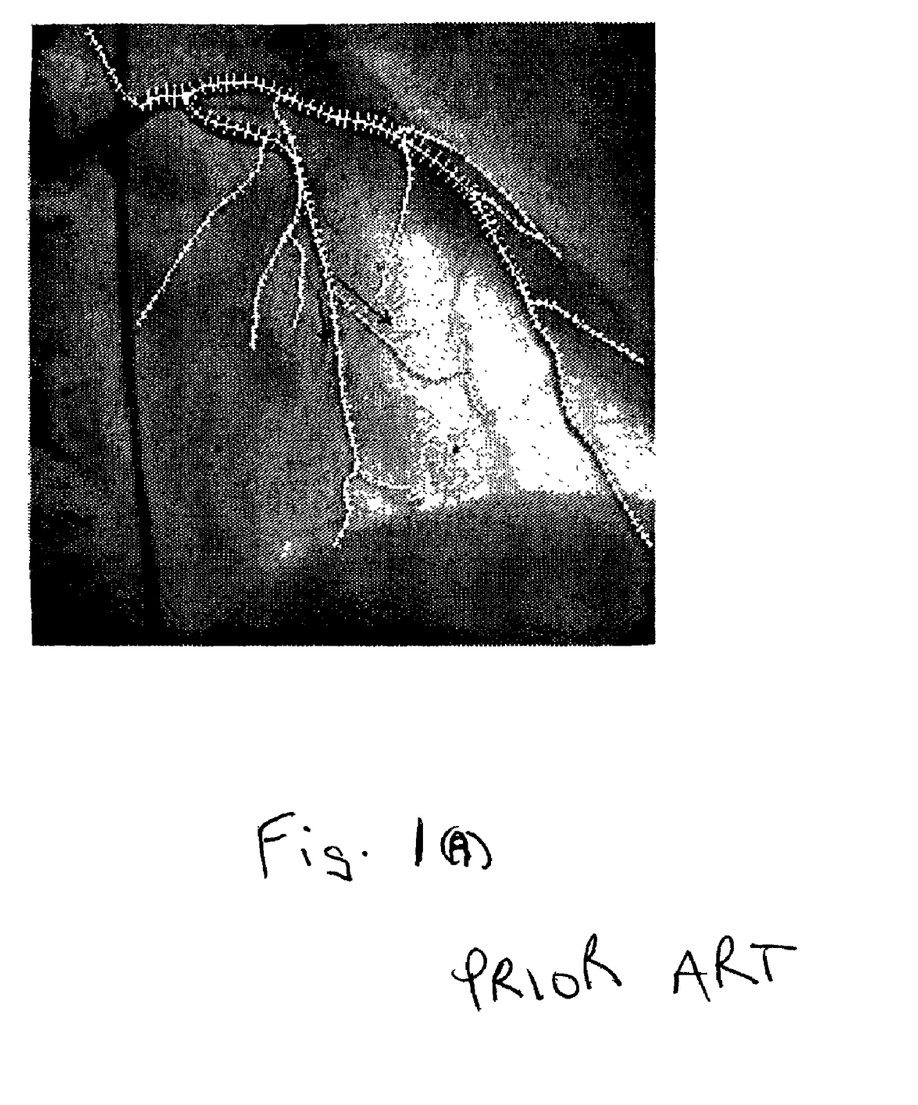
FIGS. 1(A), 1(B) show vessel features on a pair of angiograms including bifurcation points, diameters, directional vectors of bifurcations and vessel centerlines.
Figure 1B:
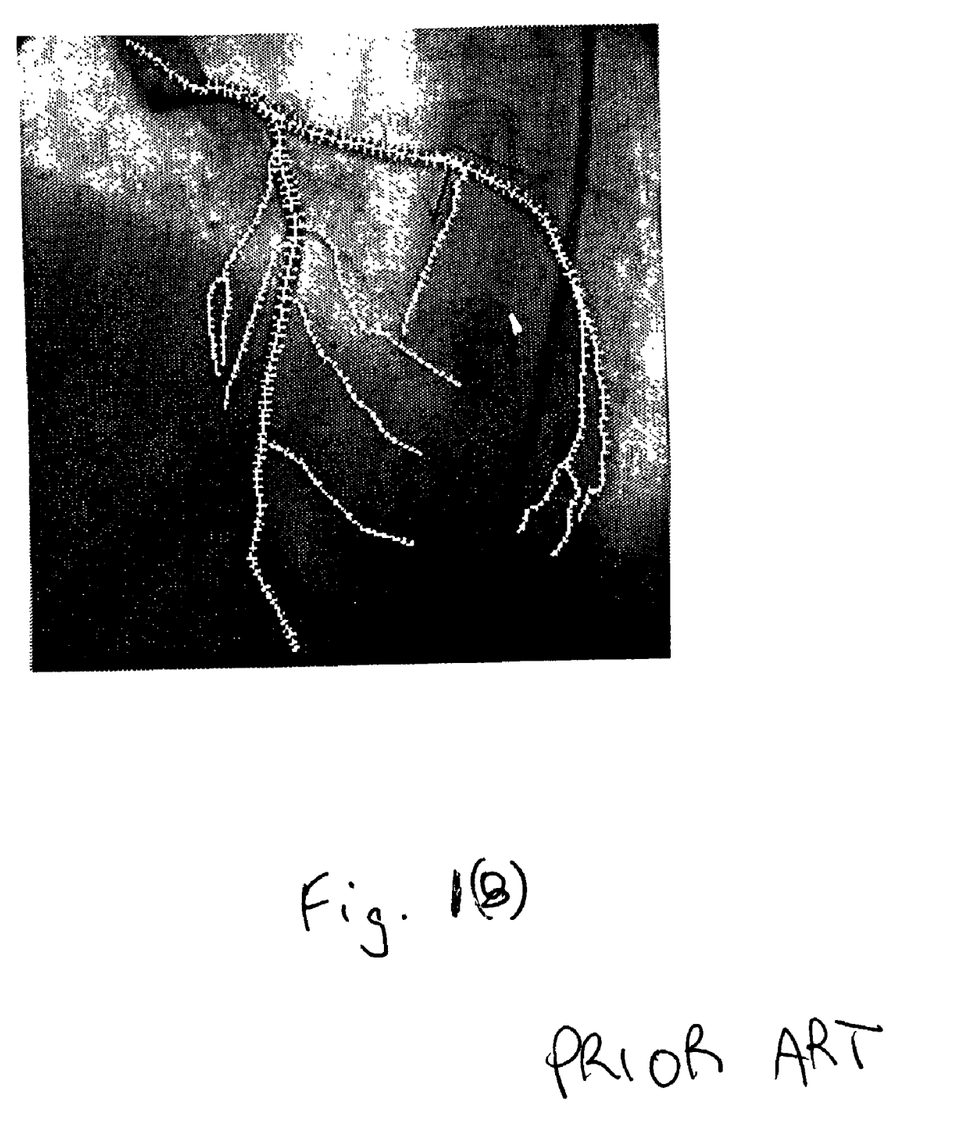

The Chen and Carroll II 2-view approach does require considerable manual editing in order to retrieve the coronary tree. As used hereinafter, the more general term 'modeling' shall be used to describe techniques which are similar to the above-described 2-view approach in that they are aimed at the construction of a schematic description of the coronary tree based on several image data acquisitions. More particularly, Chen and Carroll II teaches the use two types of optimal view maps, the foreshortening map and the overlap map, which two map types may be combined by the user to form a composite map, i.e., the 2-View map. Prior art FIGS. 1(a) and 1(b) show the extracted features including vessel diameter, bifurcation points, direction vectors and vessel centerlines of the left coronary arterial tree.

Chen and Carroll II also teaches that an on-line 3-D reconstruction technique to reconstruct the entire coronary arterial trees based on two views required from routine angiograms without need of a calibration object, and using a single-plane imaging system, as well as a new optimization algorithm realized by minimizing the image point and vector angle errors in both views subject to constraints derived from the intrinsic parameters of the single-plane imaging system.

Given the 3-D character of the coronary artery tree, Chen and Carroll II expected that any projection would foreshorten a variety of segments. A reconstructed 3-D coronary arterial tree may be rotated to any selected viewing angle yielding multiple computer-generated projections to determine for each patient which standard views are useful and which have no clinical value due to excessive overlap and foreshortening. Chen and Carroll II provide for computer-simulated projections for display with information of calculated percent foreshortening and overlap on the screen, such that a used may select any view by use of keyboard input.

The foreshortening map is an interactive map created as a composite of viewable sizes of the central vessel axis of a segment of interest for all possible viewing angles. Use of the foreshortening map renders a user able to manually explore suggested viewing positions and to manipulate the vessel model and check the corresponding position on the foreshortening map. The displayed size of the vessel or luminary organ of interest depends on the actual viewing direction of the coronary tree with respect to the position of the radiation source.

Figure 2A:
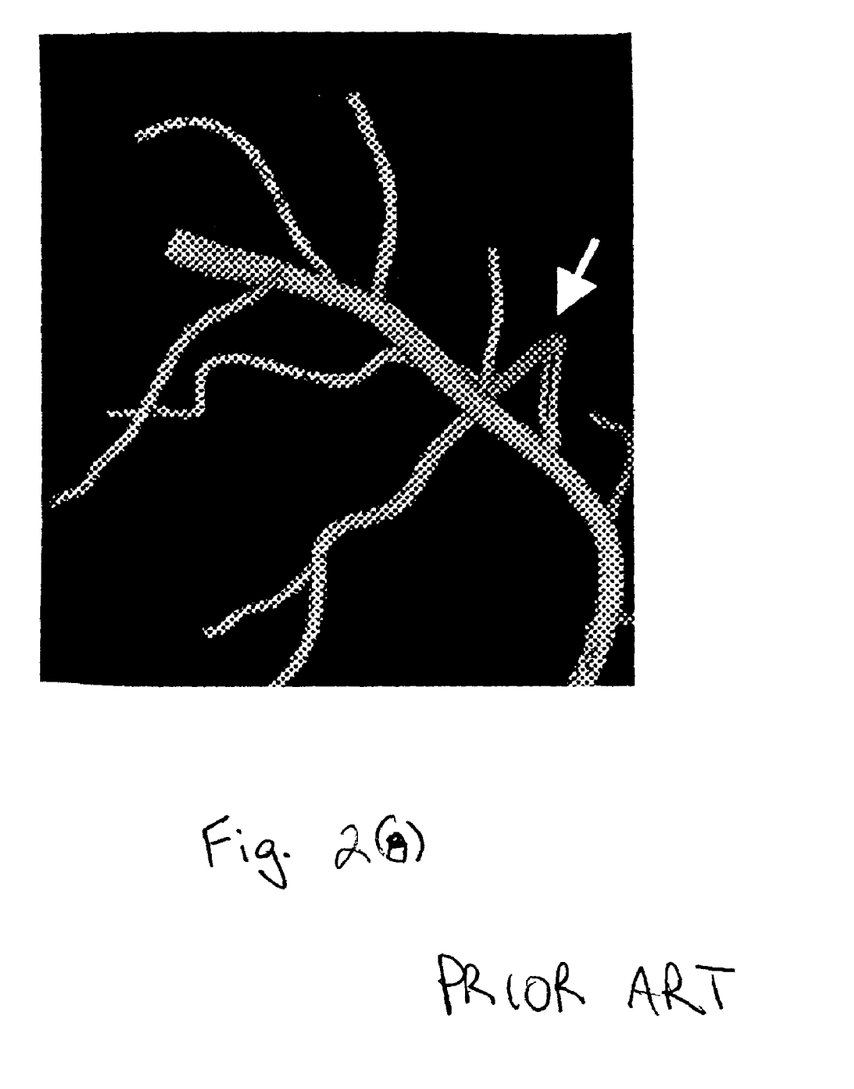
FIG. 2(A) is a 3D coronary model in which the white arrow is pointing towards a manually determined coronary segment of interest.
Figure 2B:
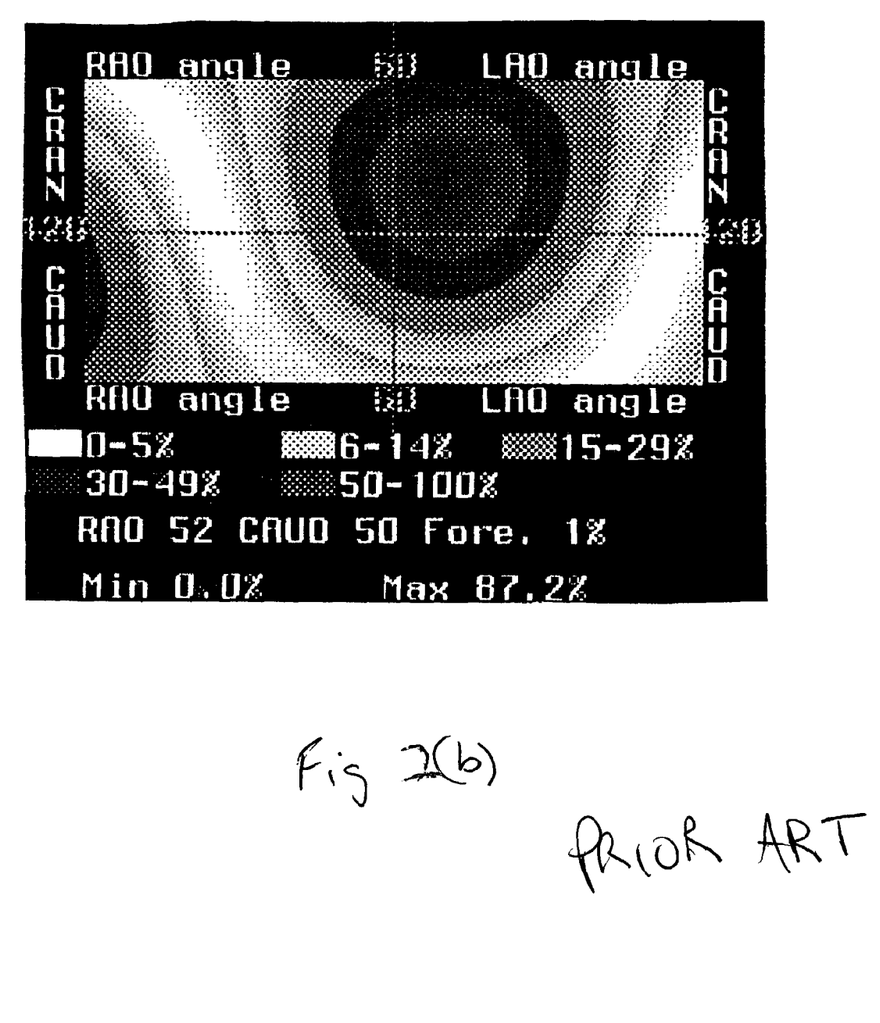
FIG. 2(B) is a foreshortening map.
Figure 2C:
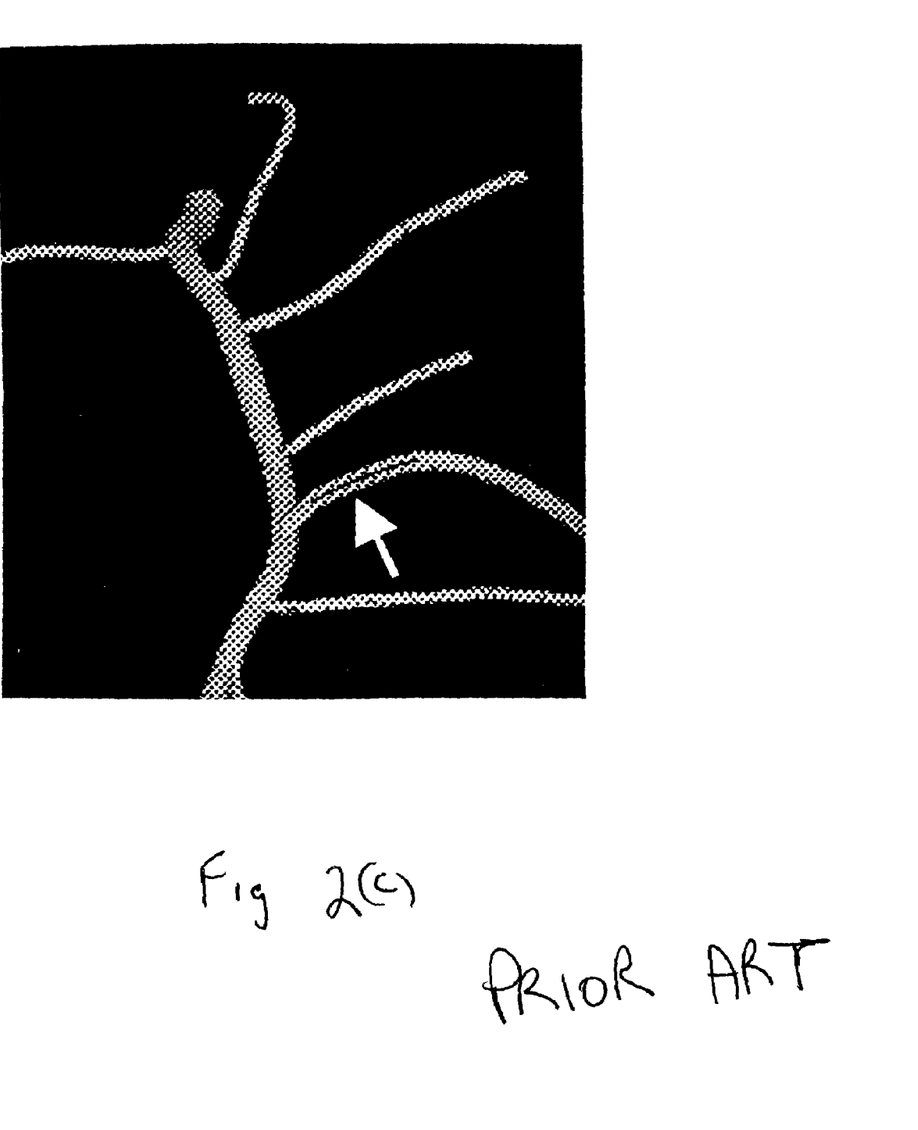
FIG. 2(C) is an optimal viewing angle of the segment shown in FIG. 2(A)

In prior art FIG. 2(a), the white arrow is arranged to point towards a manually determined coronary segment of interest. The corresponding central vessel axis is shown as a black line. Prior art FIG. 2(b) is an example of a conventional foreshortening map, which foreshortening map may be color-coded to provide a quick and intuitive overview of the viewing angles and corresponding gantry positions. Foreshortening maps minimize amounts of foreshortening, allowing for manual exploration of suggested viewing angles. An example of an optimal viewing angle for viewing a particular vessel of luminary organ is shown in prior art optimal view map of FIG. 2(c).

Figure 3A:
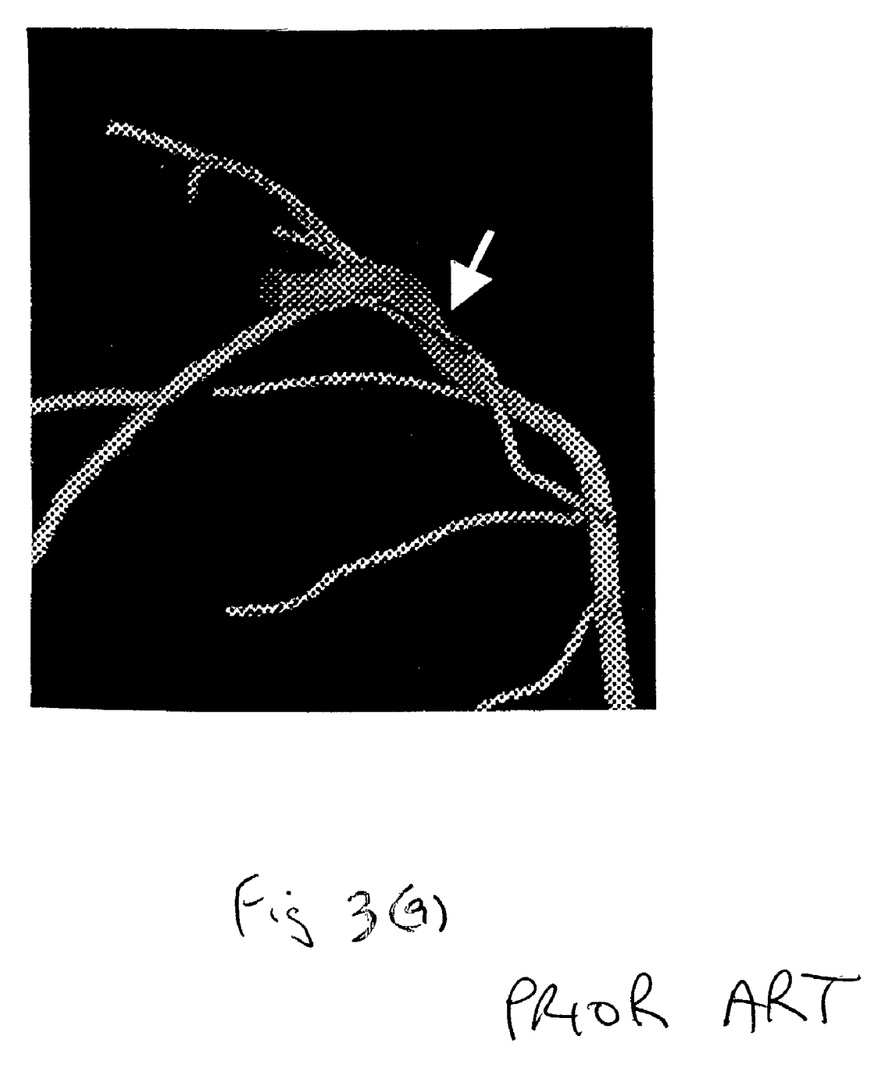
FIG. 3(A) is a map showing a viewing angle which highlights the overlap problem.
Figure 3B:
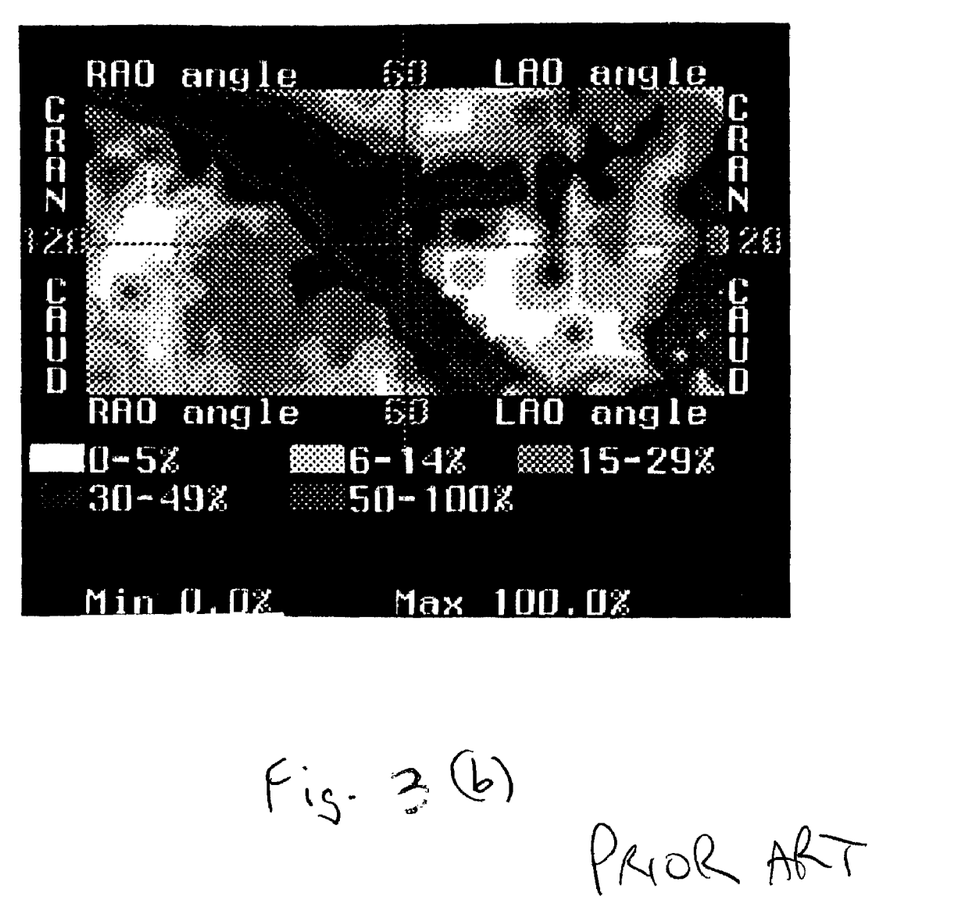
FIG. 3(B) is a map which shows an estimate of how much overlap is actually present for every viewing angle.
Figure 3C:
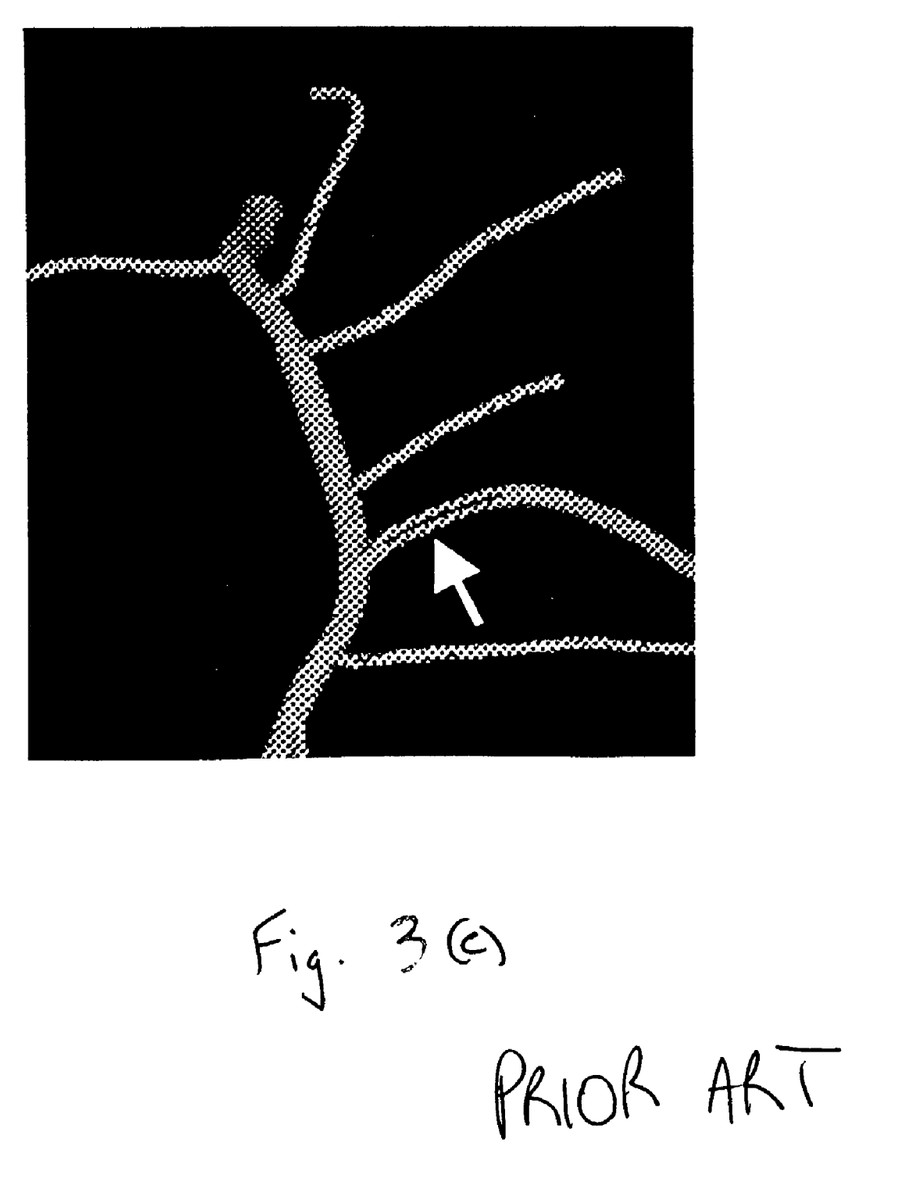
FIG. 3C is a map showing an optimal viewing angle of the segment shown in FIG. 3(A)

Next to a possible foreshortening, it is also possible that other vessel segments are overlapping the segment of interest, which case is clear by way of view shown in prior art FIG. 3(a). As a result, the operator may want to find another viewing angle in order to obtain a more clear sight (or view)

of the vessel or other lumen of interest. This type of map is referred to in the conventional arts as an overlap map. Such an overlap map provides that for every possible viewing angle an estimate may be made of how much overlap is actually present. This information is preferably color-coded, such as is set forth in an interactive table comprising FIG. 3(b). An example of the optimal viewing angle is shown in the prior art optimal view map of FIG. 3(c) (overlap).

Chen and Carroll further investigated and developed the work set forth in Chen and Carroll I. S. J. Chen and J. D. Caroll, COMPUTER ASSISTED CORONARY INTERVENTION BY USE OF ON-LINE 3D RECONSTRUCTION AND OPTIMAL VIEW STRATEGY, MICCAI 1998: 377–385 (hereafter "Chen and Carroll III"), incorporated herein by reference. Said further investigation realized the use of a composite map in addition to the foreshortening and overlap map. The coronary treatment disclosed in Chen and Carroll III sets forth a process which includes selecting an arterial segment of interest on the projection of the reconstructed 3D coronary model (for example, at an identified arterial stenosis or any veinous or nonvascular lumenary pathway blockage). Based thereon, their suggested optimal view strategic process is employed to realize a foreshortening, an overlap and a composite map.

The Chen and Carroll III composite map comprises a combination of the foreshortening and overlap maps discussed above. The maps utilized by Chen and Carroll III enable a user to interactively select arterial segments by which any computer-generated projection image associated with the gantry orientation may be previewed. More particularly, the two maps together, formed as a composite map, are said to facilitate views with minimal foreshortening and vessel overlap for the selected arterial segment in order to guide subsequent angiographic acquisitions for interventional processes.

While the Chen and Carroll III developments provide significant support for 3D viewing, selection of optimal viewing angles using their process may still present problems for the viewer, the problem becoming particularly acute when their process is used in a real-time intervention. That is, using the Chen and Carroll III view map may still limit a viewer's ability to clearly and effectively discern the position of a gantry used in image data acquisition and Chen and Carroll's foreshortening, overlap and composite maps.

SUMMARY OF THE INVENTION

It is therefore an object of the present invention to overcome the shortcomings of the present state of 3D angiographic (broadly, lumenary) visualization.

It is a further object of this invention to provide one or more additional maps for modeling lumenary, e.g., coronary arterial tree, dimensions of a patient form multiple viewing angles, which, by their use, overcome the shortcomings of the viewing processes and maps known in the prior art.

It is another object of this invention to compute an overlay without first creating a coronary tree model.

It is still another object of the invention to create an overlay map which provides a user with an ability to realize instantaneously whether a standard viewing angle will realize an appropriate view, or whether a more optimal view is preferable before acquiring an angiogram vis-à-vis the standard viewing angle.

It is still yet another object of the invention to allow a user to mark particular positions on a vascular tree to enable particular views to be more readily discernable.

The present invention proposes the formation of at least one new map, referred to hereinafter as a feasibility map. The inventive feasibility map for determining gantry positions which are possible in theory, but impossible in practice. A second new map is also disclosed and claimed hereby. The second map is a composite of the data comprising the feasibility map (Fe), a foreshortening map (F) and an overlap map (O), referred to hereinafter as an FeFO optimal view map, or FeFO OVM. Markers on the FeFO OVM serve as reference positions. For example, markers may correspond to the projection angles that are normally used in coronary angiography.

DETAILED DESCRIPTION OF THE PREFERRED EMBODIMENT

The inventive feasibility map set forth and claimed herein was devised in an attempt to model the dimensions of a patient (his/her/its actual size) where the underlying premise is that depending on the size of the patient and the configuration of the imaging device, some gantry positions which may be theoretically possible may be impossible in practice. By way of example, a patient may be modeled as half a cylinder with respect to their physical dimensions during an imaging operation. The inventive process, software, dedicated computers, workstations, etc. include a feature which will warns an user/operator once the gantry angle extends outside of the limits of a calculated optimal viewing angle.

The feasibility map may be obtained in several ways. A first method of preparing a feasibility map allows a clinician to choose from a set of preset maps depending on weight and size of a patient. Also, the map may be interactively built and maintained each time the image intensifier touches an object. More complex methods may involve the use of structured light or laser in order to derive an anatomical outline of the patient and convert same into the feasibility map.

Figure 4:
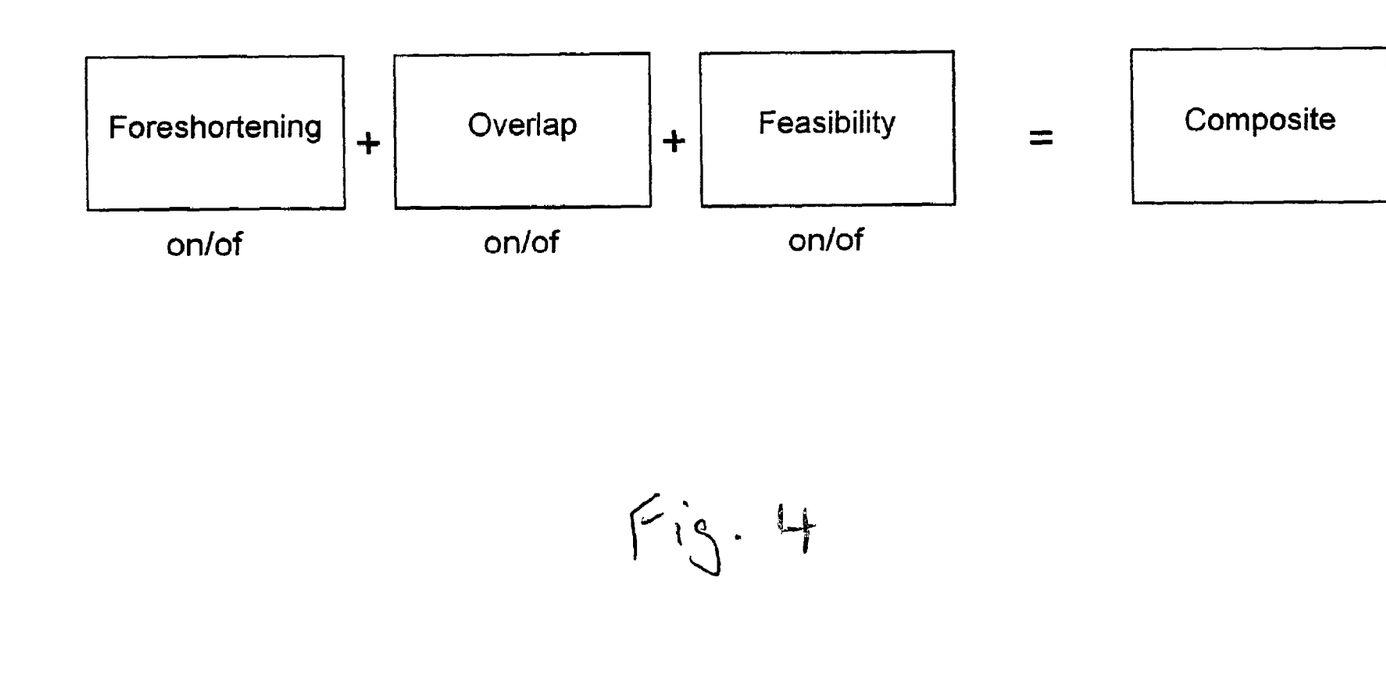
FIG. 4 highlights a first embodiment of a composite map of this invention.

The 3-view FeFO composite map or FeFO OVM, as described herein, provides a user with an ability to at all times (of course depending on the representation of the coronary tree) generate a composite of any combination of the three maps as described above. FIG. 4 highlights an ability of the present invention to generate an optimal view map from various combinations of the foreshortening, overlap and feasibility maps. Each of the three maps may be included as part of the composite, or inventive OVM, by way of either hardware directly (e.g., on/off switch), or by inclusion of a flag in the software controlling view formulation.

Figure 5A:
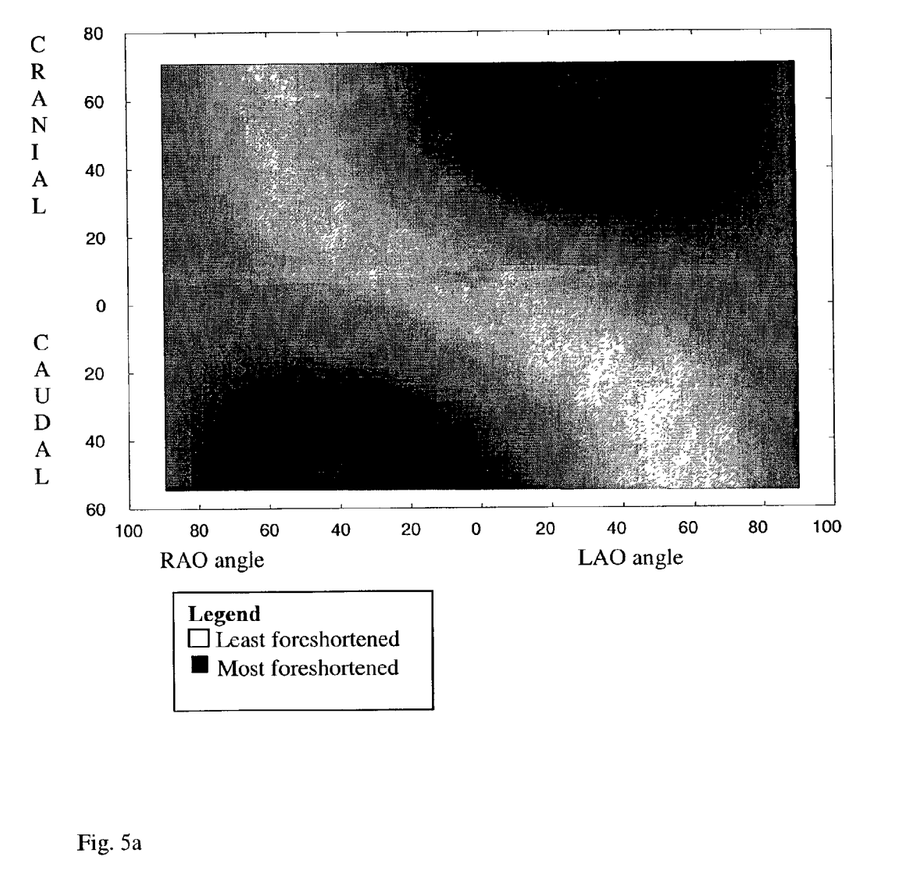
FIG. 5(A) shows a foreshortening map.
Figure 5B:
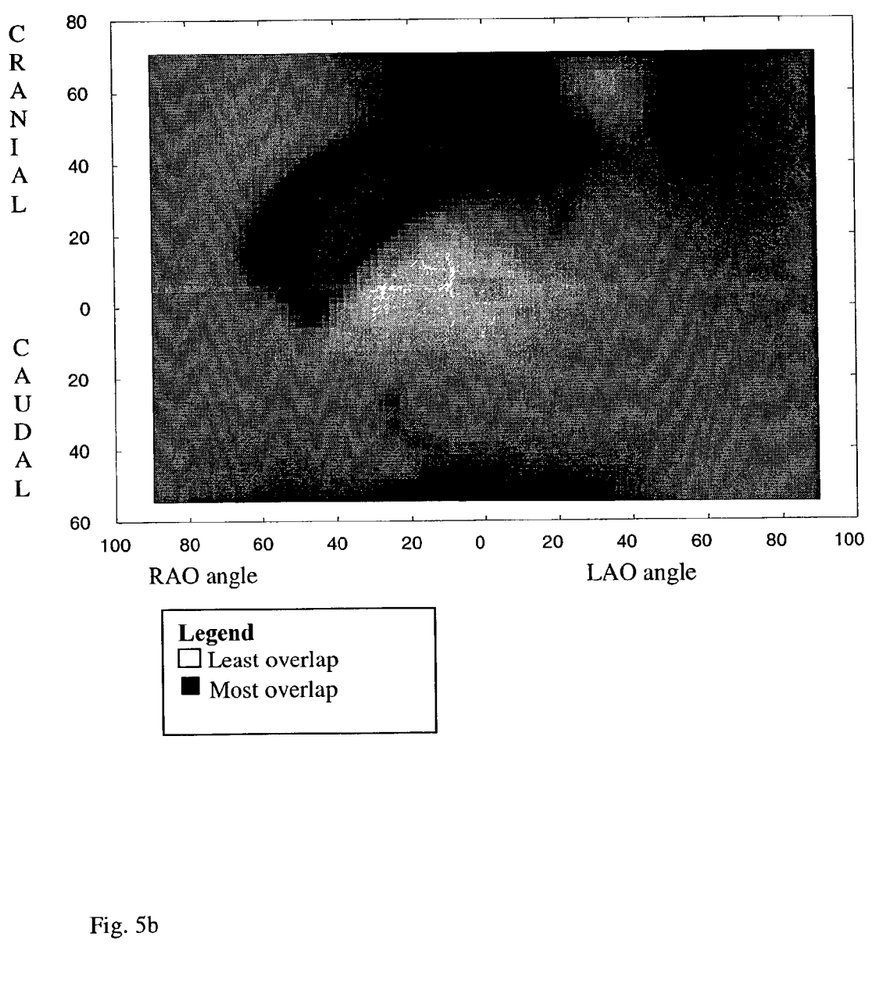
FIG. 5(B) shows an overlap map.
Figure 5C:
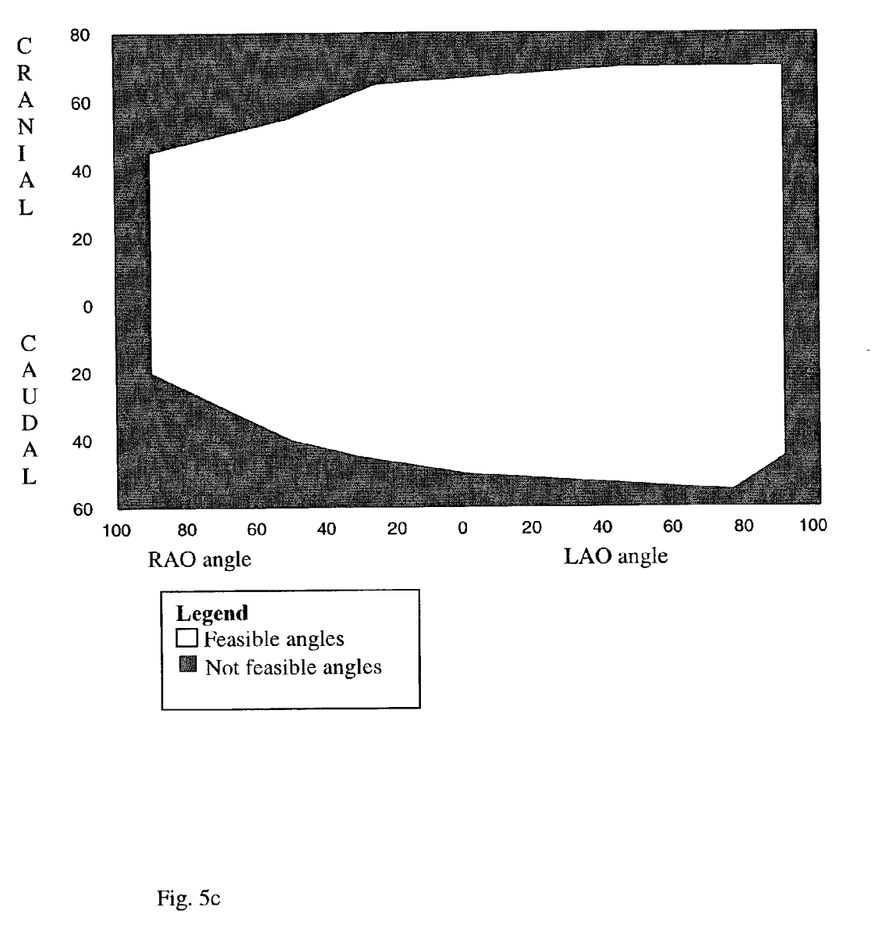
FIG. 5(C) shows a feasibility map as claimed herein.
Figure 5D:
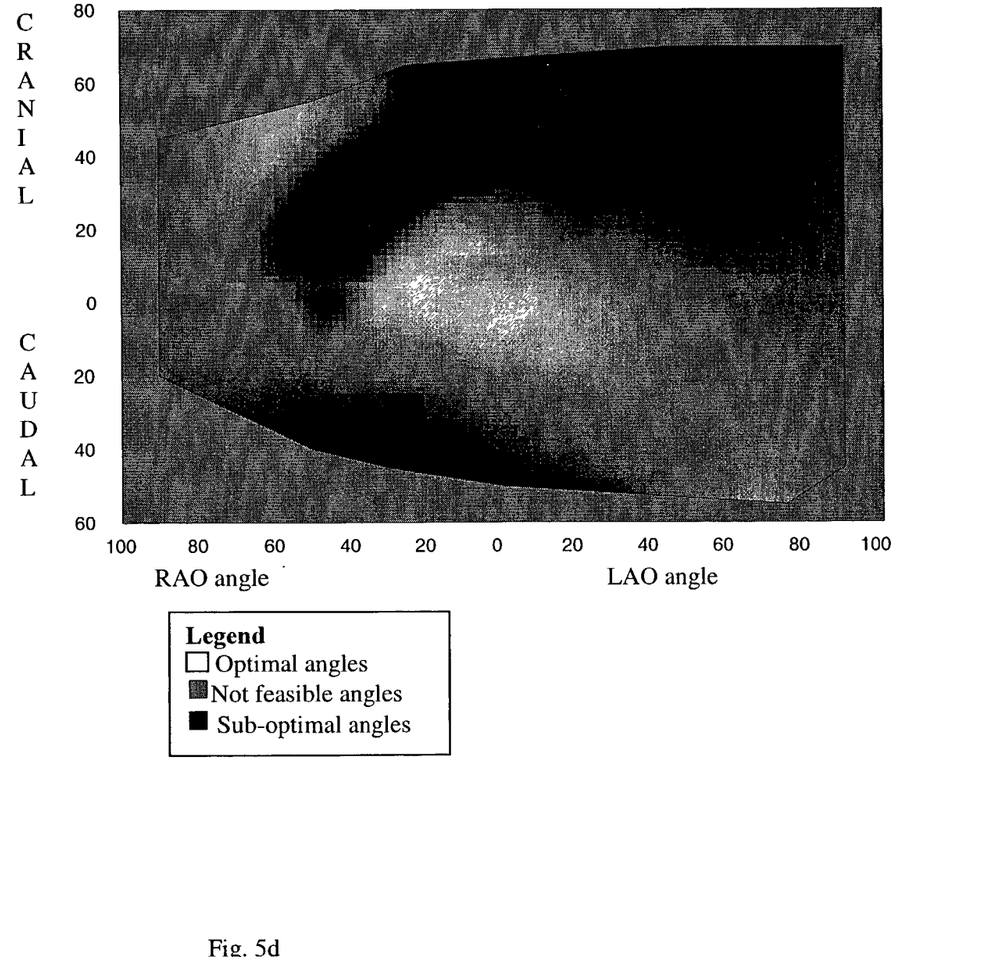
FIG. 5(D) shows an optimal view map of this invention.

FIG. 5(A) shows a foreshortening map; FIG. 5(B) shows an overlap map; FIG. 5(C) shows an artistic rendition of a proposed feasibility map of this invention; and FIG. 5(D) is a composite FeFO optimal view map. The FIGS. 5(A) and 5(B) images are first normalized (between 0 and 1) and the sum of these two maps is taken to form the OVM of FIG. 5(D). The composite may be a weighted sum, depending on the value the clinician accords the individual maps. The invention provides the clinician with an ability to toggle between various combinations of the different maps.

Symbols drawn on the optimal view map correspond to reference gantry positions, for example the standard projection directions made for routine diagnostic coronary angiograms. These symbols can be programmed according to each cardiologist's preferences individually. Moreover, a symbol drawn on the FeFO optimal view map correspond to the current orientation of the 3D model on the screen of the workstation. Said symbol concurrently moves when the volume is rotated so that it always corresponds to the angulation/rotation of the current viewing angle. Hence, the symbol moves around the FeFO OVM when the 3D model or reconstruction is rotated on screen. Note that the 3D model and the OVM may be displayed on screen simultaneously.

One skilled in the art will quickly realize that the inventive theory behind the FeFO OVM disclosed may be extended for volumetric representations of the coronaries as well. The user requires a center line of a segment of interest, i.e., a stenotic vessel segment, in order to realize a foreshortening map. The overlap map may be created by computing the projection of the model in a particular direction and detecting whether the computed center line will be overlaid by other vessel segments. Projection may be generated by means of, for example, ray casting or 3D texturing. Because overlap maps need only be derived for the vessel segment of interest, a projection of the volumetric dataset need only be calculated for those rays intersecting the vessel segment of interest.

No explicit representation of the coronaries is needed to utilize the method set forth herein. For that matter, the inventive method utilizing the FeFO OVM, and apparatus arranged to implement same, avoids the need to generate any explicit representation of a luminary pathway, e.g., vessel, under study. To calculate the foreshortening map, only the center line of the vessel segment of interest is necessary. To calculate the overlap map, in principle, the complete vessel information, derived from a 3D model, is required.

The inventions set forth herein will normally require just an estimation of a portion of a central lumenary axis, for example, the central coronary axis (CCA), in order to compute the foreshortening map. There are at least three methods that can be applied to determine the central coronary axis in the region of interest.

The first method for determining a central lumenary pathway, e.g., central coronary axis, which may be utilized is the "self-adjusting probe" method, set forth by Jan Bruijns, SEMI-AUTOMATIC SHAPE EXTRACTION FROM TUBE-LIKE GEOMETRY, Conference article, submitted by Mr. Bruijns to complement disclosure of same at a conference: Vision, Modeling and Visualization, held at {WHERE}, Germany, 2000, the article incorporated herein by reference. The self-adjusting probe method is used in shape adjusting using only a set of normalized directions on the outer surface of a central lumenary pathway or vessel, or normalized gradient directions of boundary vessel voxels.

The minimum cost path method was published in an article by Onno Wink, W. J. Niessen and M A Viergever, MINIMUM COST PATH DETERMINATION USING A SIMPLE HEURISTIC FUNCTION, International Conference on Pattern recognition, Barcelona, Spain, (date), which article is incorporated herein by reference. The third method is manual editing, well known to those practicing in the art.

While no explicit representation of the coronaries is needed to implement the inventive FeFO OVM as set forth herein, an estimate of the width of the vessels (next to the central coronary axis) in the entire volume is needed. In order to obtain the latter, there is at least one approach. That is, the use the (user-) defined intensity lookup table to segment the coronaries. Based on the (user) defined viewing parameters (level and width) it can be determined how many segments contribute to a specific viewing projection. Once a series of points in two or more angiographic projections is identified, the 3D modeling algorithm will generate the centerline.

A beneficial result from the use of the FeFO OVM is that it provides a basis for enabling a user to divide lengthy coronary artery of interest in two or three FeFO optimal view maps.

Another beneficial result from the use of the FeFO OVM of this invention is an ability to simulate corresponding projection. This is particularly useful where the FeFO OVM is based on a reconstructed image. That is, practice has found it to be advantageous to simulate a chosen projection before any actual acquisition is performed. In addition, a user may use the invention to calculate compute two FeFO optimal view maps for different vessel segments of interest in the same patient, and combine these into a combined optimal view map that gives optimal result for both vessel segments.

Yet another beneficial result realized from use of the FeFO OVM of this invention is that it overcomes some of the problems associated with optimally viewing bifurcations. That is, instead of computing the different maps on a single coronary axis, the whole process can be applied for a bifurcation as well. By use of the inventive FeFO OVM, it is not very difficult to implement for a bifurcation once the general framework already exists.

Still another basic advantage of the FEFO OVM of this invention is its use in calculating desirable default viewing angles. The standard viewing angles that are traditionally used in coronary imaging can be (programmed) and positioned in the FeFO optimal view map to form a reference for the clinician. And still another basic advantage of the FeFO OVM of this invention is its ability to provide feedback to the imaging device. Once a viewing angle is determined on the 3D RA workstation, it would be very convenient if the imaging device could be automatically configured to obtain the corresponding projection image.

What is claimed is:

1. A method for optimally viewing a portion of a patient vascular system to facilitate at least one of diagnosis and treatment of said vascular system, the method comprising the steps of:

acquiring a model of said vascular system based on image data generated by an imaging device;

identifying a portion of interest of said vascular system including determining a central vessel axis for a vessel of interest;

generating a foreshortening map of the portion of interest based on viewing angle and imaging device position, with respect to the patient;

generating an overlap map to determine an amount of overlap for particular viewing angles based on imaging device position; and generating a feasibility map to model dimensions of the patient based on size of the patient, imaging device configuration, foreshortening and overlap.

2. A method for optimally viewing a portion of a patient vascular system to facilitate at least one of diagnosis and treatment of said vascular system, the method comprising the steps of:

acquiring a model of said vascular system based on image data generated by an imaging device;

identifying a portion of interest of said vascular system including determining a central vessel axis for a vessel of interest;

generating a foreshortening map of the portion of interest based on viewing angle and imaging device position, with respect to the patient;

generating an overlap map to determine an amount of overlap for particular viewing angles based on imaging device position;

generating a feasibility map to model dimensions of the patient based on patient characteristics, imaging device configuration, foreshortening and overlap; and generating a composite view of said segment of interest in accordance with said foreshortening, feasibility and overlap maps.

3. A method as set forth in claim 2, wherein said step of generating a composite view includes generating an optimal view map in accordance with said composite view.

4. A method as set forth in claim 1, wherein said segment of interest may be identified with at least one marker for viewability.

5. A method as set forth in claim 4, wherein an optimal view of said optimal view map is generated automatically.

6. The method of claim 1, wherein the step of generating a feasibility map serves to eliminate, based on said size and said configuration, gantry position determinations for said viewing that would theoretically be possible if said size and said configuration were not taken into account.

7. The method of claim 1, wherein the step of generating a feasibility map takes into account that some gantry positions are theoretically possible but infeasible in practice.

* * * * *